United States Patent [19]
Grabner et al.

[11] Patent Number: 6,045,503
[45] Date of Patent: Apr. 4, 2000

[54] METHOD OF AND APPARATUS FOR DETERMINING THE TOPOLOGY OF A CORNEA

[75] Inventors: Günther Grabner, Vienna; Reinhard Eilmsteiner, Weiselburg; Wolgang Husinsky, Vienna, all of Austria

[73] Assignee: Kamilllo Eisner-Stiftung, Hergiswill / NW, Switzerland

[21] Appl. No.: 09/234,212

[22] Filed: Jan. 20, 1999

[51] Int. Cl.7 ..................................................... A61B 3/16
[52] U.S. Cl. ........................................... 600/405; 351/212
[58] Field of Search ..................... 351/211, 212, 351/221, 202; 600/405, 400, 404, 399, 401

[56] References Cited

U.S. PATENT DOCUMENTS 5,307,096  4/1994  Baroth et al. ........................... 351/212
5,355,884  10/1994  Bennett ..................................... 600/405
5,830,139  11/1998  Abreu ....................................... 600/405

FOREIGN PATENT DOCUMENTS

400 664  2/1996  Austria .

*Primary Examiner*—George Manuel
*Attorney, Agent, or Firm*—Henry M. Feiereisen

[57] ABSTRACT

A method of analyzing the condition of a cornea by employing a probe for indenting the cornea. The topology of each indentation is registered and processed in the form of images and/or displayed on a monitor. A analyzing apparatus for carrying out the method includes a video keratoscope which has attached thereon a positioning device comprised of electromotive drives and adjustment members, for moving the probe.

42 Claims, 8 Drawing Sheets

METHOD OF AND APPARATUS FOR DETERMINING THE TOPOLOGY OF A CORNEA

BACKGROUND OF THE INVENTION

The present invention relates to a method and apparatus for determining the topology of a cornea.

Austrian Pat. No. 400 664 discloses an apparatus for analyzing the topology of the cornea, in particular for in vivo or in vitro assessment of the curvature of the anterior surface of the cornea. The analyzing apparatus includes a video keratoscope which uses the conventional placido-process to detect corneal distortion by reflecting alternating black and white rings onto the anterior corneal surface. A support arm is mounted on a motor-operated feed table and carries a contact member or probe. The feed table together with the support arm is so advanced by linear motors in the direction of the cornea that in a first phase (zero position), the probe is moved in position in respect to the cornea without effecting corneal deformation, and in a second phase, the probe is moved toward the cornea to realize an indentation in the μm range. In the first phase, an image is taken of the curvature of the cornea, and after indentation by means of the probe, the operator photographs momentary distortion of the corneal surface. By comparing the images, the determined topographic deviations enable the operator to infer to local, pathological changes of the cornea and to determine possible corneal distortions.

SUMMARY OF THE INVENTION

It is thus an object of the present invention to provide an improved method and apparatus for carrying out the method for sequentially determine relevant characteristics, in particular topographic characteristics of a cornea, and to provide data to facilitate the decision process for possible surgery, transplantation and for recognition, in particular early diagnosis of various corneal diseases.

This object, and others which will become apparent hereinafter, are attained in accordance with the present invention by forming a first image of the natural topography of a cornea, indenting at least one area of the cornea by a probe to effect a momentary deformation of the anterior corneal surface, forming a second image of the deformation of the anterior corneal surface, measuring the deformation to produce commensurate topological-dependent data, processing and storing the data for identifying property of the cornea, and signaling in the form of visual and/or acoustic means to an operator the data for diagnostic evaluation of the corneal topography.

An Apparatus for determining topological data of a cornea to be analyzed, includes a positioning device, driven by an electromotor, a mounting having one end secured to the positioning device and another end, a probe supported by the other end of the mounting and having a pointed end for applying an indentation force on the cornea to realize a deformation of the anterior corneal surface, an electromagnet positioned between the mounting and the probe and so interacting with the probe as to withdraw the probe from a sphere of influence of the electromagnet to thereby disengage the pointed end from the anterior corneal surface when the indentation force exceeds a predetermined level, and a detection system, e.g. a keratoscope having a projection cone and detection means for determining and measuring a deformation of the anterior corneal surface realized by the probe during indentation of the cornea.

Through the method and apparatus in accordance with the present invention, the ophthalmologist is now able to carry out a precise analysis before eye surgery, in particular before a refractive surgery of the cornea, by determining the mechanical properties of the cornea as dependent from the thickness and elasticity (E-modulus) as well as local variations, whereby these properties are of particular relevance for determination of the surgical procedures.

Advantageously, the indentations and the determination of the topology-dependent data can be executed pulse-synchronous for each patient so that the sequential imaging is realized in synchronism with the heart beat. Thus, possible falsification as a consequence of pulse-based motions of the eye are practically eliminated.

Data formulated on the basis of the analysis and parameters derived from the data provide a basis for an early recognition of certain pathological changes of the cornea that impair the eyesight and may be used as pre-surgical and post-surgical information for an analysis of the corneal topography. Thus, the novel and inventive method and apparatus allows the application of a dynamic analysis of the cornea (DCI=Dynamic Corneal Imaging).

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Throughout all the Figures, same or corresponding elements are generally indicated by same reference numerals.

Figure 1:
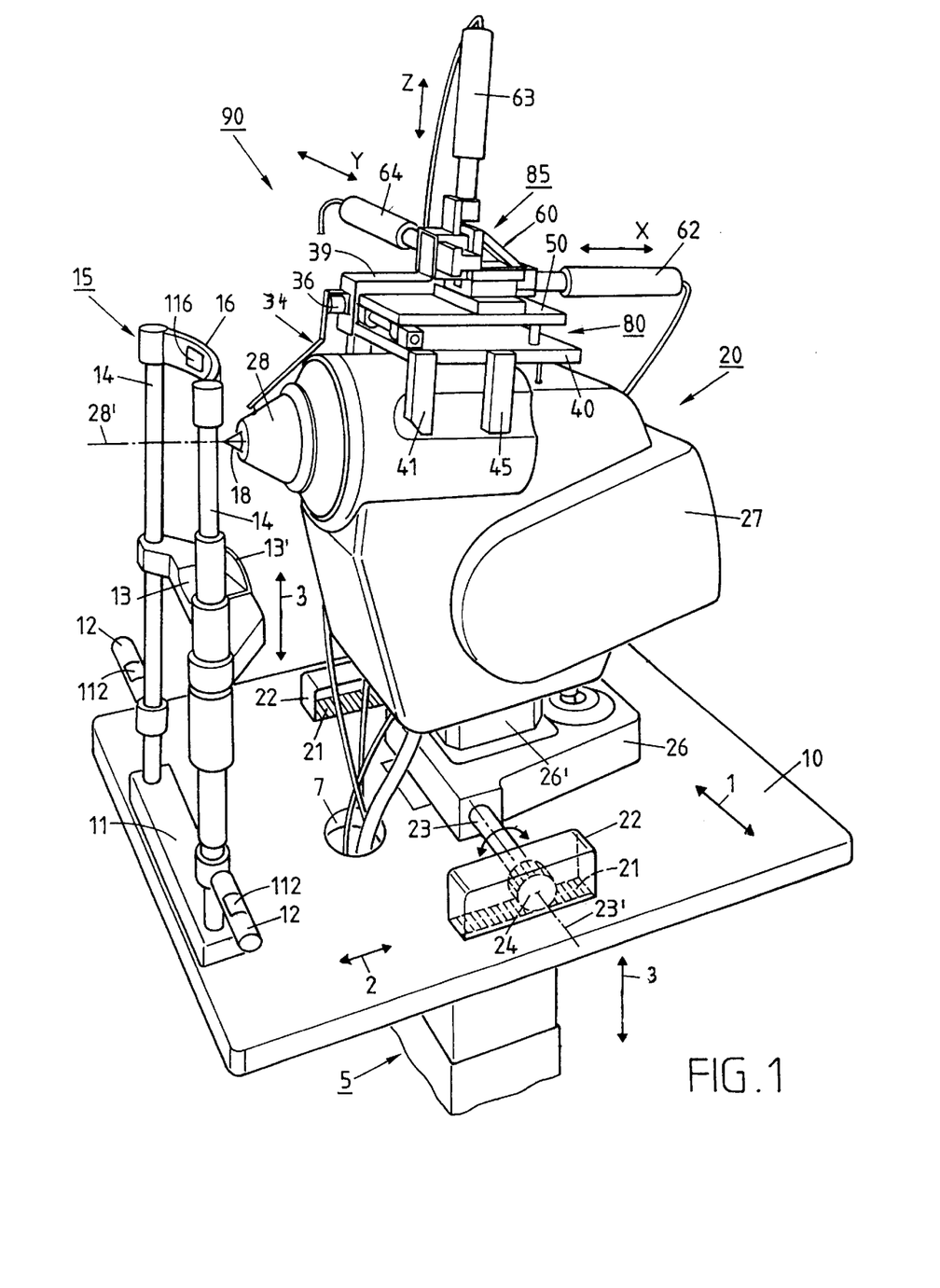
FIG. 1 is a front and side perspective view of an apparatus for determining the topology of an anterior surface of a cornea, in accordance with the present invention.

Turning now to the drawing, and in particular to FIG. 1, there is shown a front and side perspective view of an analyzing apparatus in accordance with the present invention, generally designated by reference numeral 90 for primarily in vivo analysis of the state of a cornea 18 (FIG. 8) by ascertaining the shape of the anterior corneal surface before and after indentation to thereby draw a conclusion about the condition of the cornea. It will be understood by persons skilled in the art that in vitro analysis is certainly also possible, for example analysis of a donor cornea. In this case, the donor cornea being analyzed is mounted, preferably before implantation, on a suitable holder for subsequent indentation.

The analyzing apparatus 90 includes a platform 10 which is supported by a telescopic stand 5 for placement on the ground. Although not shown in detail in the drawings, the stand 5 may have incorporated therein a hydraulic or pneumatic lifting device to shift the platform 10 in vertical direction of double arrow 3. Certainly, it is also possible to manually shift the platform 10.

Placed on the platform 10 near an edge thereof is a head support frame, generally designated by reference numeral 15 and secured onto the platform 10 by a mount 11. The frame 15 includes two parallel uprights 14 spaced from each other and secured at their lower end on the mount 11. Attached near the lower end of each upright 14 is a handle 12 which has incorporated therein a sensor 112. Extending approximately in a central area between the uprights 14 of the frame 15 is a support 13 for placement of a patient's chin. The chin support 13 is formed with a terminal plate 13' for proper positioning of the patient's chin. Suitably, the chin support 15 may include an electromotor (not shown) for displacement in direction of double arrow 3, or the displacement may be realized manually, to thereby best suit the position of the patient. Extending across the top of the upright 14 is a support 16 for the patient's forehead. The forehead support 16 is preferably configured in arched or convex shape to suit to the patient's forehead and also accommodates a sensor 116.

At a distance to the head support frame 15 is a conventional keratoscope, e.g. a video keratoscope, generally designated by reference numeral 20 for detecting the contour or topography of the cornea. A suitable video keratoscope is commercially available under the trademark KERATRON® or available under the trade name Optikon/Rom. Such video keratoscopes typically use a placido disk with associated light source for projection of alternating opaque black and white rings onto the anterior surface of the cornea to thereby enable an operator to detect corneal distortions. Other methods are certainly also applicable within the scope of the present invention, such as rasterstereo-photogrammetry or interferometry.

Figures 8, 9:
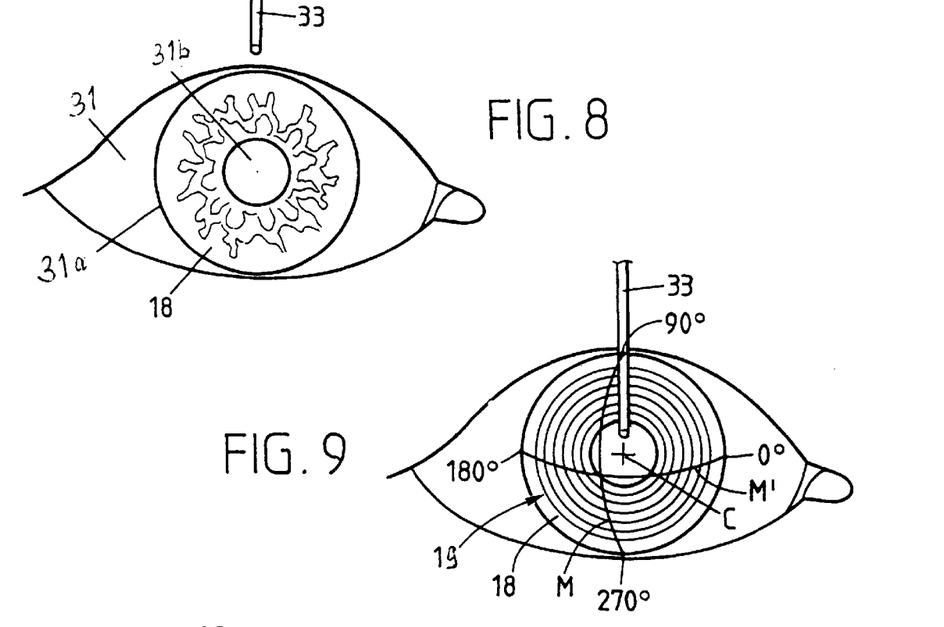
FIG. 8 is a schematic illustration of a human eye with partial illustration of the probe.
FIG. 9 is a schematic illustration of the eye with placido rings reflected onto the anterior surface of the cornea and with the probe in a first position for indentation.
Figures 10, 11:
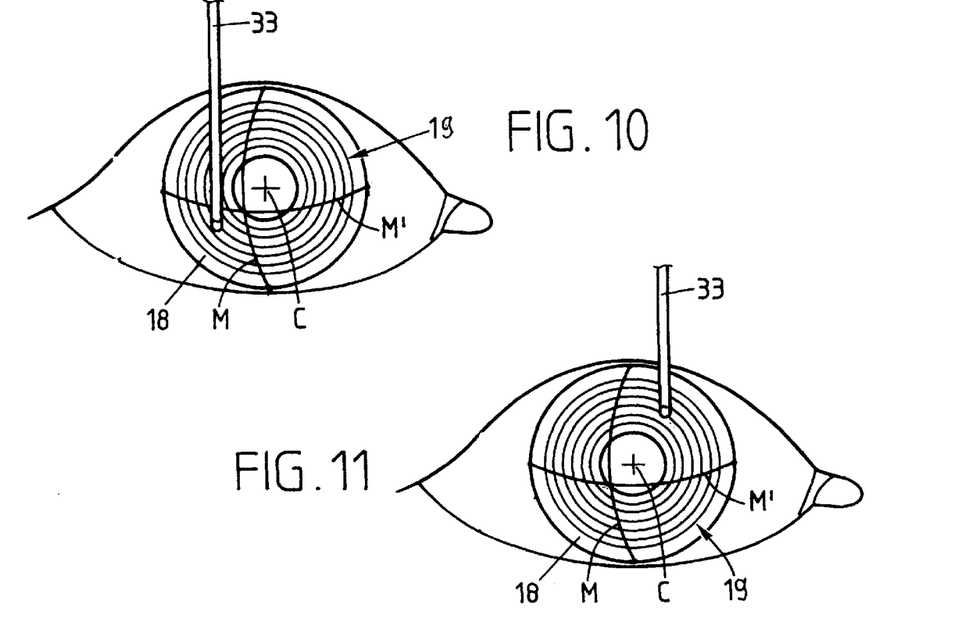
FIG. 10 is a schematic illustration of the eye with reflected placido rings and with the probe in a second position for indentation.
FIG. 11 is a schematic illustration of the eye with reflected placido rings and with the probe in a third position for indentation.

In the nonlimiting example of FIG. 1, the video keratoscope 20 operates with a transparent placibo disk and includes a conical projector 28 (measuring head) with associated light source for projecting a number of rings impervious to light onto the anterior surface of the cornea 18 of a human eye, as shown in FIGS. 8 to 10. The projector 28 is defined by an optical axis 28', with the rings being formed concentric and equidistant to the optical axis 28', whereby the contour of the rings reflected onto the cornea 18 changes in dependence on the topography of the cornea being analyzed.

Figure 2:
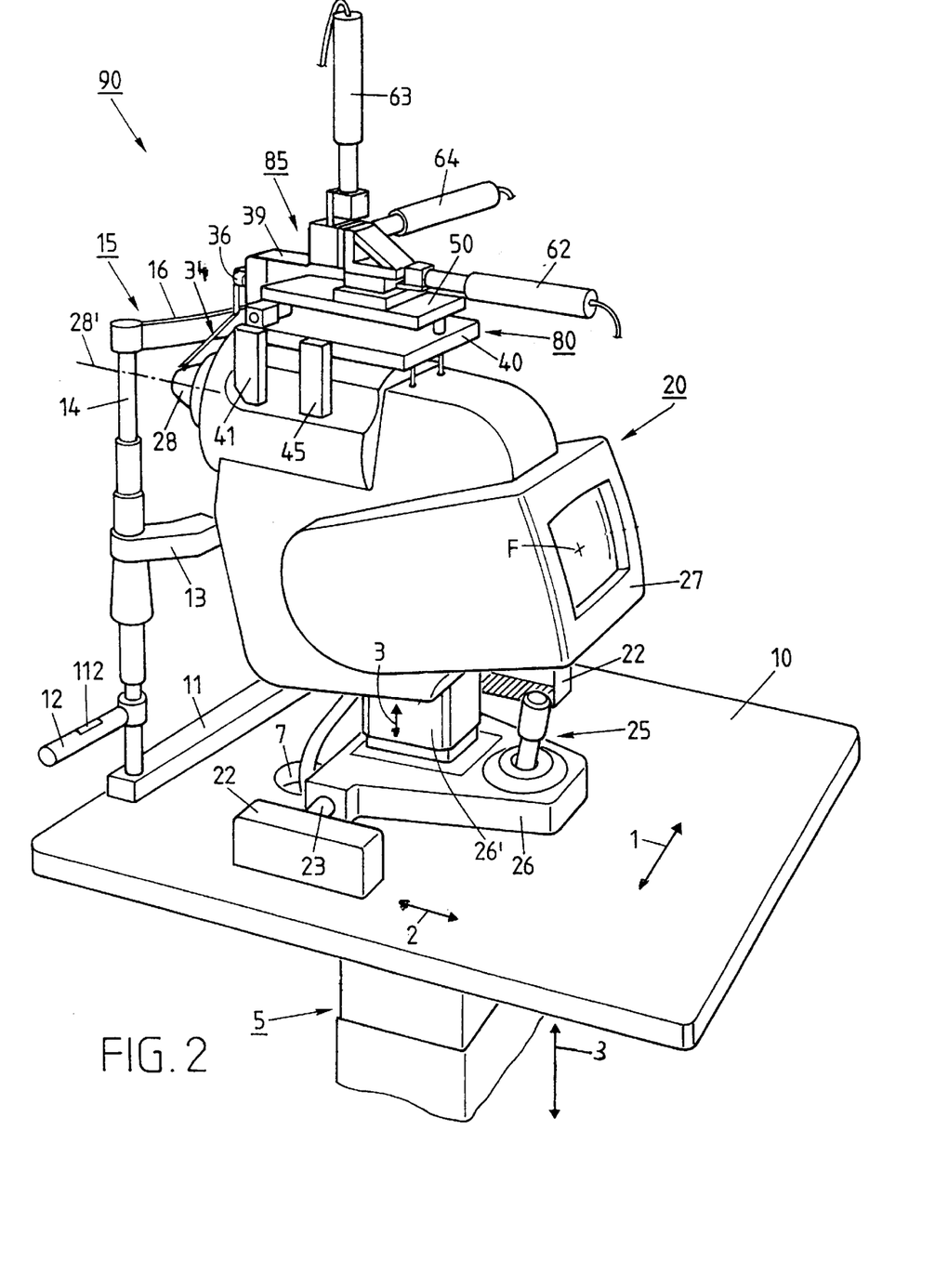
FIG. 2 is a rear and side perspective view of the apparatus of FIG. 1.

The video keratoscope 20 includes a monitor 27 which is mounted on a stand 26 for placement on the platform 10 which is formed with an opening 7 for feedthrough of necessary cables for the keratoscope 20. The stand 26 includes a telescopic support 26' for allowing a positional readjustment of the keratoscope 20 in vertical direction of double arrow 3. The stand 26 accommodates a shaft 23 which projects on both ends thereof out from the stand 26, with each shaft end carrying a roller 24 (only one is shown in FIG. 1) for travel along a rack 21. For safety concerns, each roller 24 with associated rack 21 is housed in a box 22 which is mounted on the platform 10. The shaft 23 is suitably operated by an electromotor (not shown) which is incorporated in the stand 26 and controlled by a joystick 25 (cf. FIG. 2) extending out of the stand 26 to permit the operator to displace the keratoscope 20 in the horizontal direction of double arrow 2 relative to the head-support frame 15 or patient and in the horizontal direction of double arrow I for focusing purposes as well as in vertical direction of double arrow 3, whereby a displacement of the chin support 13 in either direction of double arrow 3 ensures a precise alignment of the theoretical optical axis 28' of the projector 28 with respect to the patient's eye. The alignment of the optical axis of the respective eye with the optical axis 28' of the projector 28 is realized by means of a fixation point provided in the center of the projector 28 and focused on by the patient during examination. By means of the joystick 25, the operator can thus move the video keratoscope 20 in three dimensions to thereby align and advance the projector 28 with the cornea 18 of the patient's eye.

It will be appreciated by persons skilled in the art that the keratoscope 20 must contain much mechanical components which does not appear in the foregoing Figures. However, these components are not part of the invention, and have been omitted from the Figures for the sake of simplicity.

Secured on the video keratoscope 20 is a positioning device, generally designated by reference numeral 85 for accurately controlling the position of a probe 33 (FIG. 3) inside the projector 28. As shown in particular in FIG. 4, which is a view of the positioning device 85 in direction of arrow IV in FIG. 3, the probe 33 projects through an opening 29 into the beam path 28" of the projector 28. The opening 29 is suitably so dimensioned that the probe 33 can be adjusted horizontally in longitudinal direction with respect to the theoretical optical axis 28' of the projector 28 and in predetermined spatial ranges and thus, the probe 33 can be advanced toward the cornea 18 for indentation in a number of randomly selected positions.

Figure 3:
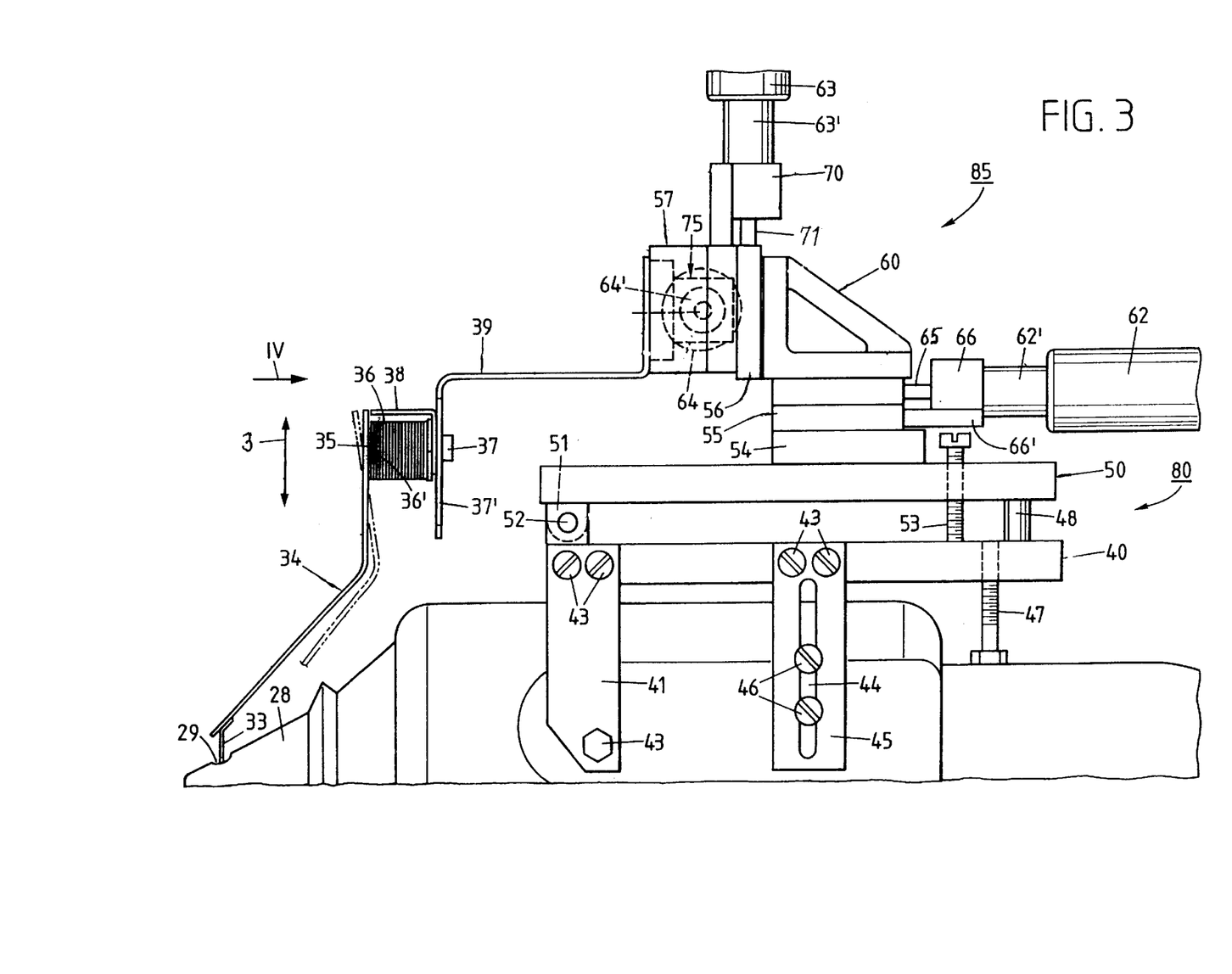
FIG. 3 is a fragmented side view, on an enlarged scale, of the apparatus of FIG. 1, illustrating in detail a positioning device for a probe.

The positioning device 85 includes three electromotive drives 62, 63, 64, for example micromotors, which are disposed along the axes of a three-dimensional coordinate system for adjustment of the probe 33 in direction of double arrows X, Y, Z via associated adjustment members 55, 56, 57 (FIG. 3). The probe 33 is secured to one end of a support arm 34 which is made preferably from a profiled body of rectangular cross section and of relative rigid design. Secured near the other end of the support arm 34 is a knob 35 of ferromagnetic material for engagement in a recess 36' (FIG. 3) of an electromagnet 36 which is attached to an angle 38 and secured to a bracket 39 of substantially Z-shaped configuration by a screw fastener 37 which is received in an oblong hole 37' in the bracket 37 for manual positional adjustment in vertical direction of arrow 3 with respect to the theoretic optical axis 28' of the projector 28. The bracket 39 is detachably mounted, e.g. by screw fasteners (not shown) to a confronting end face of the adjustment member 57, as shown in FIG. 3.

The support arm 34 and the probe 33 are preferably made of electrically conductive material and held in place in dependence on the force exerted by the electromagnet 36 for indenting the cornea 18. For example, the probe 33 may be made of a relative thin wire, preferably of non-corrosive steel, so that a disinfecting cleansing of the probe 33 is possible after each use. As the support arm 34 can be easily detached from the electromagnet 36, the cleansing of the probe 33 is simple, without need for any auxiliary tools.

The required operating current for the electromagnet 36 can be so adjusted that the support arm 34 together with the probe 33 automatically swigs away from the zone of influence of the electromagnet 36, as indicated by dashdot line in FIG. 3, to thereby disengage the pointed end 32 (cf. FIG. 4) of the probe 33 from the cornea 18 when a predetermined and accordingly set indentation force is exceeded. In this manner, possible malfunctions of the analyzing apparatus 90 will not cause harm to the patient. Suitably, the pointed end 32 of the probe 33 is formed with an absolutely smooth end face, e.g. in flat, rounded or hemispherical configuration, to prevent damage or injury of the cornea 18. Other configurations of the pointed end 32 of the probe 33 and variations of the cross section of the probe (diameter or the like) of the probe 33 are certainly also possible and within the scope of the present invention.

The positioning device 85 is mounted to the keratoscope 20 by a carrier unit, generally designated by reference numeral 80 and including a base plate 40 which is mounted by a first type of supports 41 and a second type of supports 45 on opposite sides to the keratoscope 20 and secured by screw fasteners 43. The supports 45 have formed therein an oblong slot 44 for permitting a pivoting of the base plate 40 relative to the monitor 27 by means of an adjustment screw 47, preferably two in spaced-apart disposition, near the rear end of the base plate 40. The adjustment screws 47 are threadably received in complementary bores of the base plate 40 and supported by the monitor 27. Actuation of the adjustment screws 47 result in a displacement of the base plate 40, whereby screws 46, which engage the slots 44 of the supports 45, secure the base plate 40 in place.

Figure 4:
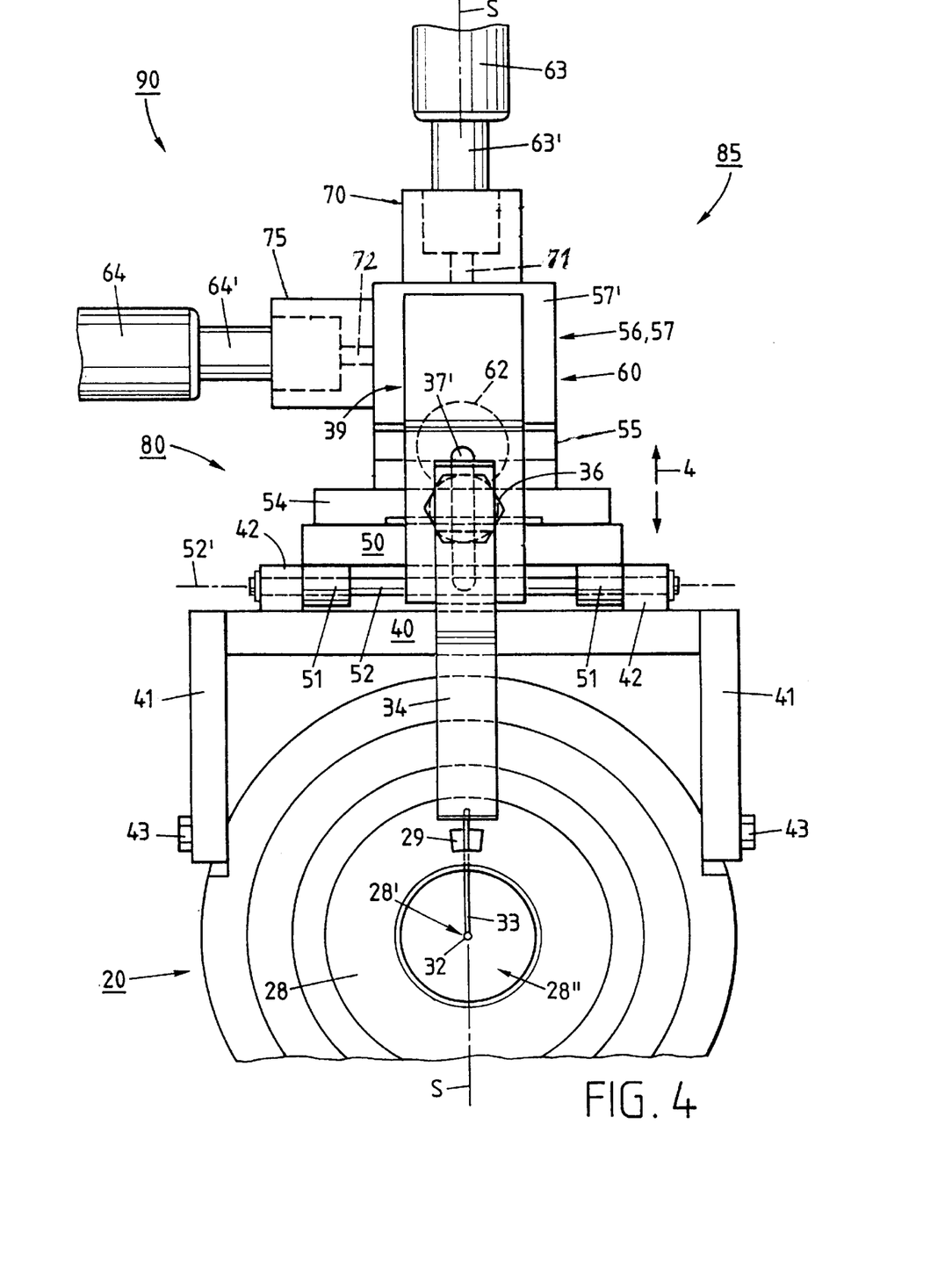
FIG. 4 is a view of the positioning device, taken in the direction of arrow IV in FIG. 3.

Extending at a distance to the base plate 40 is a top plate 50 which is pivotally mounted at its front end to the base plate 40 by mounts 51 and swingably attached to a bolt 52 for rotation about an axis 52' (FIG. 4). Near its rearward end, the top plate 50 has spaced-apart boreholes for receiving adjusting screws 53 by which the top plate 50 can be pivoted relative to the base plate 40 by a certain range about the axis 52'. Suitably, the base plate 40 and the top plate 50 extend parallel to one another and are held in place by the adjusting screws 53, whereby a, preferably spring-elastic, spacer 48 extends between the plates 40, 50 near their rear end.

As best seen in FIGS. 3 and 4, the top plate 50 has mounted thereon a pedestal 54 for support of a bearing block 66 which receives a journal 62' of the electromotive drive 62 of the positioning device 85 and operatively connects the electromotive drive 62 with the associated adjustment member 55 via a dog 65. Suitably, the adjustment member 55 is detachably secured by a screw connection (not shown) to the pedestal 54. Mounted onto the pedestal-distal side of the adjustment member 55 is a horizontal leg of an angle bracket 60. The vertical leg of the angle bracket 60 has mounted thereon the adjustment member 56 which is operatively connected to the electromotive drive 63 of the positioning device 85 via a bearing block 70 which receives a journal 63' of the electromotive drive 63 for connection to the adjustment member 56 via a dog 71. In like manner, the adjustment member 57 is operatively connected to the electromotive drive 64 via a bearing block 75 which receives the journal 64' of the electromotive drive 64 for engagement with the adjustment member 57 via a dog 72, as shown in particular in FIG. 4.

Suitably, the electromotive drives 62, 63, 64 are arranged as a structural unit on the top plate 50 and realize a highly accurate displacement of the adjustment members 55, 56, 57 in $\mu$m range in the direction of arrows X, Y, Z and of the interacting probe 33, support arm 34, electromagnet 36 and bracket 39. The positioning device 85 arranged on the top plate 50 may be moved or pivoted by the adjusting screws 53 in a certain range about the axis 52' of the bolt 52 relative to the base plate 40 for positioning the probe 33 relative to the optical axis 28' of the projector 28 and for indenting the cornea 18, as will be further described in more detail with reference to FIGS. 6 and 7 furtherbelow.

Although, as shown in FIG. 4, the electromotive drive 64 is arranged on the side of the interacting adjustment member 57 with respect to an axis of symmetry S, it is certainly within the scope of the present invention to place the electromotive drive on the opposite side of the axis of symmetry S. Also, it is certainly possible to incorporate a fourth electromotive drive in opposition to the electromotive drive 64.

Figure 5:
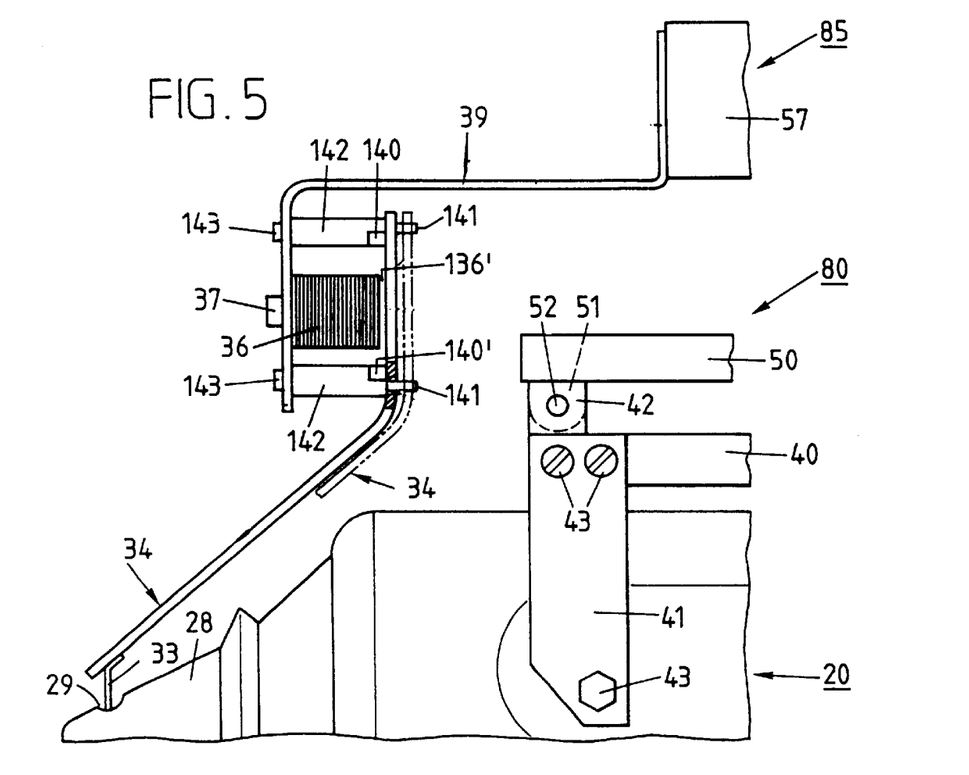
FIG. 5 is a fragmented side view, on an enlarged scale, of a modification of the apparatus of FIG. 1, illustrating in detail a modified support unit for carrying the probe extending into a projector.

Turning now to FIG. 5, there is shown a fragmented side view, on an enlarged scale, of a modification of the analyzing apparatus 90, with the difference to the embodiment of FIG. 1 residing primarily in the support of the probe 33. The probe 33 is secured on one end to the support arm 34 which, in comparison to the embodiment shown in FIG. 1, extends less steeply and is curved toward the other end as to extend in closer proximity to the carrier unit 80. Positioned parallel to the curved end of the support arm 34 is one end section of the substantially Z-shaped bracket 39 which has a prolonged middle section so as to extend outwardly from the curved end of the support arm 34. The other end section of the bracket 39 is secured to the adjustment member 57, shown only partially. Extending between the confronting sections of the bracket 39 and the support arm 34 are two spaced supports 142 in the form of, for example, cylindrical bolts, which are secured to the bracket 39 by screw fasteners 143. On their screw fastener distal end, each bolt 142 is formed with an outwardly projecting pin 141 which is received in a complementary bore of the support arm 34 for carrying the support arm 34. Secured by suitable means, preferably detachably, to each of the bolts 142 is a force sensor 140 which is shown only schematically.

The electromagnet 36 is mounted on one end by screw fastener 37 to the bracket 39 between the bolts 142. The other end of the electromagnet 36 is positioned at a distance to the confronting section of the support arm 34 to define an air gap 136' therebetween. Suitably, the support arm 34 and the probe 33 are made of electrically conducting material and held on the electromagnet 36 in dependence on the force adjustable for indentation of the cornea 18. The set force can be monitored by the force sensors 140. Upon detecting application of an excessive force, the support arm 34 may be shifted out of the area of influence of the electromagnet 36 along the pins 141 into a position shown by dashdot line in FIG. 5, to thereby disengage the pointed end 32 of the probe 33 from the cornea 18. The shift of the pointed end 32 relative to the cornea 18 ranges in the order of 0.2 to 0.5 mm.

Figure 6:
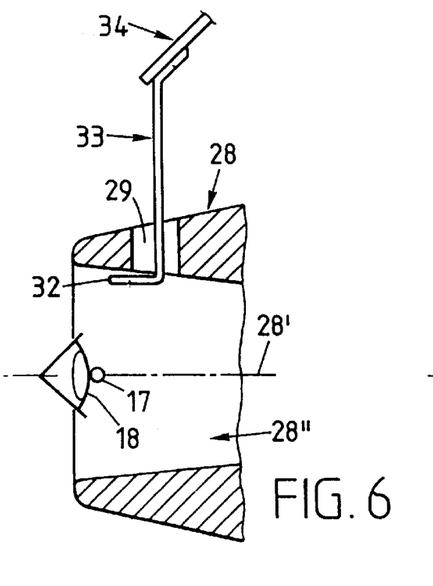
FIG. 6 is a cutaway view, on an enlarged scale, of the projector, with the probe positioned outside a path of rays generated by the keratoscope in direction of the cornea.
Figure 7:
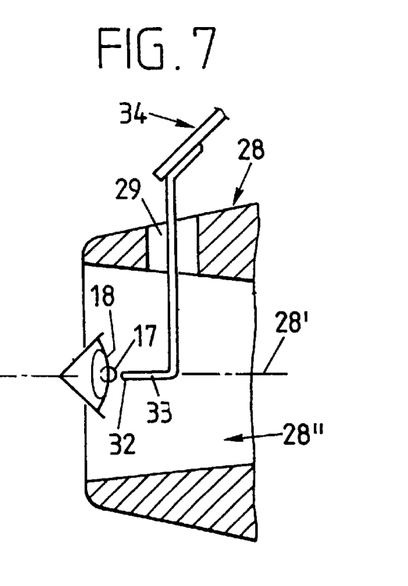
FIG. 7 is a cutaway view, on an enlarged scale, of the projector, with the probe positioned in the path of rays generated by the keratoscope in direction of the cornea.

Turning now to FIGS. 6 and 7, there are shown two positions of the probe 33 in relation to the optical axis 28'. In FIG. 6, the support arm 34 and the attached probe 33 are positioned for taking a first image of the topography of the cornea 18 outside the viewing range. In FIG. 7, the support arm 34 is so shifted by the positioning device 85 inwardly into the projector 28 that the probe 33 projects in to the beam path 28" of the projector 28 and is aligned with the theoretic optical axis 28' of the patient's eye in a randomly selected position. Suitably, the projector 28 has incorporated therein a light sensor 17, preferably an infrared light sensor, which is shown only schematically.

Turning now to FIGS. 8 to 11, there are shown schematic illustrations of a human eye with placido rings 19 reflected onto the anterior surface of the cornea 18 concentrically with respect to the theoretic center C, and with the probe 33 occupying three different positions for indentation. FIG. 8 shows a typical human eye with sclera 31, limbus 31a, cornea 18 and pupil 31b, with the probe 33 in idle position. In FIG. 9, the probe 33 is moved from the idle position into a first, randomly selected portion for carrying out an indentation of the cornea 18. Subsequently, the probe 33 can be repositioned in other randomly selected positions for indentation, as indicated in FIGS. 10 and 11. The displacement of the probe 33 into the individual positions can be realized, while maintaining a sufficient distance to the cornea 18, by shifting either parallel to the first, substantially vertical meridian M between 90° and 270°, or approximately parallel to the second horizontal meridian M' between 0° and 180°.

After positioning the probe 33 at a distance to the cornea 18 in the various positions, described in connection with FIGS. 9 to 11, the probe 33 projecting into the beam path 28" of the projector 28 is moved in a second phase from the cornea-distal position linearly in the direction of the theoretic optical axis 28' and advanced to the apex of the cornea 18 for executing the actual indentation. The locally defined indentation of the cornea 18, as selected by the ophthalmologist, causes a local concave deformation in the respective area of the cornea 18. The force N (newton) predetermined in dependence on the state of the cornea 18 and/or the feed distance selected in several stages, e.g. in increments in the order of 100, 200, 300, 400, 500 and 800 $\mu$ (micron) as selected for the indentation is so chosen by the ophthalmologist and set by suitably means that the indentation is program-controlled automatically, without any auxiliary means, by the electromotive drives 62, 63, 64.

As stated above, the feed motion as well as the return motion of the support arm 34 and the probe 33 in directions of arrows X, Y, Z are realized by the positioning device 85, whereby the electromotive drive 63 effects the movement during the first phase approximately parallel to the substantially parallel meridian M between 90° and 270°, and the electromotive drive 64 effects the movement of the probe 33 approximately parallel to the horizontal meridian M' between 0° and 180° (FIG. 9). The electromotive drive 62 effects exclusively the feed motion of the probe 33 for the actual indentation of the cornea 18 essentially in the direction of the optical axis 28" of the projector 28.

The electromotive drives 62, 63, 64 are preferably controlled and activated separately and activated for executing the individual movement phases. After conclusion of the indentation, the probe 33 is withdrawn away from the cornea 18 by the electromotive drive 62. A further indentation is realized by renewed spatial alignment of the probe 33 and advance of the probe 33 toward the cornea 18 in opposite direction. The control of the electromotive drives 62, 63, 64 is so realized that a transversal motion of the probe 33 is eliminated when the probe 33 is placed on and contacts the cornea 18.

The analyzing apparatus 90 is further provided with an evaluating or processing unit 95 which receives signals in response to the successive contacts of the probe 33 upon different sites of the cornea 18. The processing unit 95 is shown by way of a block diagram in FIG. 12, and includes a detector 110, an control or interface unit 125 operatively connected to the electromotive drives 62, 63, 64 and provided as interface, and a processor 150 which is also operatively connected to the positioning device 85. Further connected to the processor 150 is a printer 154, preferably a color printer, for printing the topography of the cornea 18, as taken by a (not shown) camera, preferably in the form of single or sequential images (single images, film, true photos, false color photo or the like), and a color monitor 155 for visually illustrating, preferably in color, the functions executed in the processor 150. The handle sensors 112 and the head support sensor 116 for the patient are connected to the detector 110.

The detector 110 interacts via suitable control means 145 with the probe 33 and the electromagnet 36 to register the respective contact of the pointed end 32 of the probe 33 upon the cornea 18. In the event, the force sensors 140 are provided, as shown in the embodiment of FIG. 5, the information registered by the force sensors 140 is also inputted into the detector 110, as indicated by broken line. The control means 145 regulates and adjusts through respective signals the current supplied across the electromagnet 36 either fixedly or in dependence on the processor 150.

Figure 12:
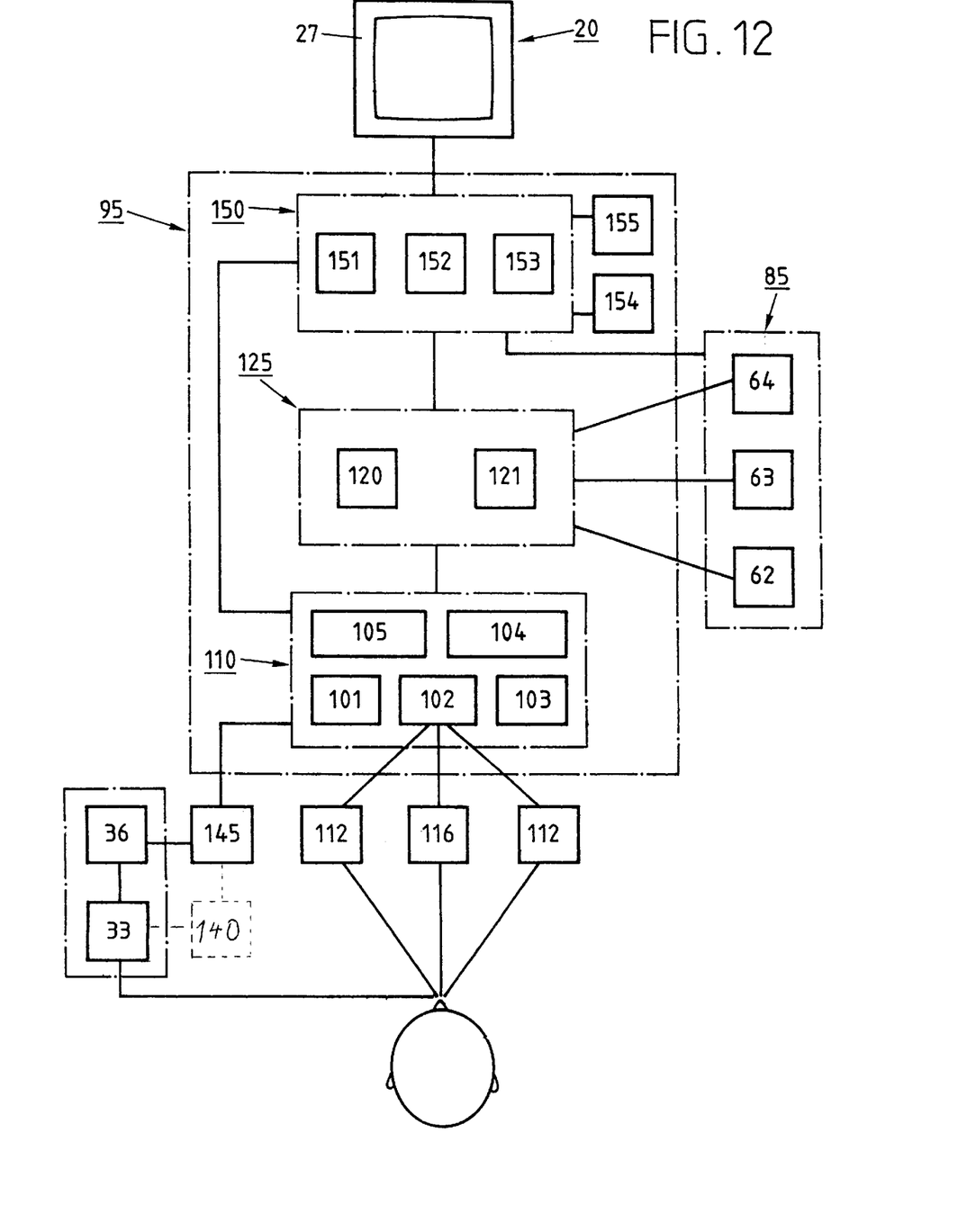
FIG. 12 is a block diagram of the apparatus for determining the topology of an anterior surface of a cornea.

The detector 110 forms an essential component for realizing the single functional steps, and includes a plurality of electrically interconnected electronic components comprised of at least one oscillator 101, at least one amplifier 102, at least one rectifier 103, at least one frequency filter 104, and a comparator 105. In order to recognize a patient, a signal, e.g. a audiofrequency signal is generated with a voltage of 12 volt and a frequency of about 4500 Hertz and applied across the handles 12, or alternatively connected via an ear clip or ECG contact with the patient. The connection by means of the ear clip or ECG contact is suitably applied for patients without limbs.

The processor 150 in conjunction with the detector 110 registers and stores pules-synchronously the corneal topography as a result of indentations carried out in increments of 100, 200, 300, 400, 500 or 800 $\mu$. The sequentially registered data of the corneal topography are registered, preferably in phase with the heart beat of the patient in order to eliminate false data as a result of the heart beat. When the patient touches both sensors 112, or one of the sensors 112 and the sensor 116, or one of the sensors 112 and the probe 33, corresponding signals are registered by the detector 110, filtered and compared with two or more values. These comparisons result in the following states "active" or "inactive" or "error", which are processed as signals and transmitted to the processor 150. These self-diagnostic states ensure further, necessary safety aspects of the analyzing apparatus 90. When an error occurs, the control program is so activated as to interrupt an ongoing examination, or the ongoing examination is halted manually immediately. When a system error occurs or when the measured value of force, pulse etc. is too high or too low, the electromagnet 36 is de-activated, to thereby immediately interrupt the ongoing examination.

For self-diagnostics, the detector 110 is so configured as to register the contact of the probe 33 on the cornea 18 and possible faulty operation. Such faulty operations, e.g. excessive force on the cornea 18 of the eye, or lack of contact with the cornea 18, or tilting of the probe 33, can be transmitted through respective signals to the processor 150 and/or displayed as readable information to the ophthalmologist on the monitor 27.

The control unit 125 interacts with the three electromotive drives 62, 63, 64 of the positioning device 85 and with the processor 150, and includes essentially a controller 120 and a so-called driver 121 for processing the signals received by the positioning device 85 and further transmission of the signals to the processor 150.

The processor 150 includes essentially a frame grabber 151, a control unit or converter 152 and a control module or controller 153. The frame grabber 151 has preferably incorporated therein optronic (optic/electronic) sensors for registering the images of the corneal topography during individual indentations and storing the images for example for further processing. The converter 152 evaluates the signals transmitted by the sensors of the frame grabber 151 and adjusts the required electric current supplied across the electromagnet 36. The controller 136 controls the operation of the electromotive drives 62, 63, 64 and registers the data of the detector 110.

The mode of operation of the analyzing apparatus 90 for determining the topology of the cornea is as follows:

In a first phase, the keratoscope 20 with the projector 28 are so positioned by the ophthalmologist with respect to the patient's eye being examined that a cross hair F inscribed on the monitor 27 of the keratoscope 20 coincides with the theoretic center C of the eye. In dependence on the cornea 18 being analyzed, the local position and depth of the indentation and/or force of indentation being carried out is determined, for example, in increments and subsequently, the probe 33 is moved by the program-controlled electromotive drives 62, 63, 64 into a pre-selected initial position, as shown e.g. in FIGS. 9 to 11.

Precondition for the above-referred dynamic analysis of the cornea 18 (dynamic corneal imaging (DCI)) resides in the exact disposition of the patient who activates at least with one hand one of the sensors 112 and with the forehead the sensor 116. The ophthalmologist moves the keratoscope 20 with the projector 28 into the so-called focus position so that the patient's cornea 18 penetrates about half of the light beam (not shown) generated by the light sensor 17 inside the projector 28. This ensures the necessary size and focus of the images (photos) made before and during indentation of the cornea 18.

A first image of the cornea 18 to be indented and analyzed may be taken without or with the probe 33 which extends into the projector 28. In the first variation, when positioning the probe 33 in the initial position at a distance to the cornea 18, as shown e.g. in FIGS. 6 and 8, in which the probe 33 is shifted upwardly with respect to the optical axis 28' of the projector 28 out of the visual range of the not shown camera of the keratoscope 20, a first image of the natural topography of the cornea is taken and stored. In the second variation, the probe 33 is moved, while the sensors 112 or sensor 116 are already activated, from the initial position in the direction of the optical axis 28' until touching the cornea 18 or the lachrymal film. This triggers a corresponding signal to take and store the first image of the natural topography of the cornea 18.

As soon as its desired position is reached, the probe 33 is moved solely by the electromotive drive 62 in the direction of the cornea 18 for subsequent locally predetermined indentation and thereafter further advanced to reach the selected depth of indentation and/or force of indentation. After the probe 33 effects the local depth of indentation and/or force of indentation upon the cornea 18, the video camera is activated and a further image is taken from the locally indented, momentary contour (topography). Further pre-selected sites of the cornea 18 are successively indented by the probe 33 and the ensuing concave indentations are registered respectively, preferably through photography. The depth of indentation and/or force of indentation applied by the probe 33 may be effected by the motor-dependent and controlled feed movement of the probe 33 or by the adjustable and observable force. The set force is monitored by the probe 33 or force sensor 140 (FIG. 5), respectively, operatively connected with the detector 110.

As soon as all sites are indented on the cornea 18 by the probe 33, as predetermined by the ophthalmologist in accordance with a program and corresponding data is generated, the probe 33 is returned to its initial position. When withdrawing the probe 33 from the cornea 18, a visual information may be displayed on the color monitor 155 and/or one or more acoustic signals may be triggered. It is important to note that the indentation of the cornea 18 is realized solely by the electromotive drive 62 in direction of the optical axis 28' along arrow X. The other electromotive drives 63, 64 are idle in this operational phase so as to eliminate a transversal movement of the probe 33 bearing upon the cornea 18.

The deformation effected by the probe 33 during indentation and thus the momentary topology of the cornea 18 is registered, and mathematically processible data are derived from the individual topographies and stored in the form of visual and/or acoustic means which can be reproduced for the actual analysis of the cornea 18.

Data derived from the individual topographies of the indented cornea 18 in the form of acoustic signals can be converted by the processor 150 on a sequence of numbers, whereby, for example, the amplitude of the signal is measured in periodically or intermittently and stored as number. Furthermore, there is the possibility to dissect the various fractions of given waves of the signal being analyzed into deep and high sounds. Preferably, an acoustic signal is generated from the information (height and curvature etc,) along a certain radius of the cornea 18, with the generated sound being simulated and reproduced in the processor 150.

Figure 13:
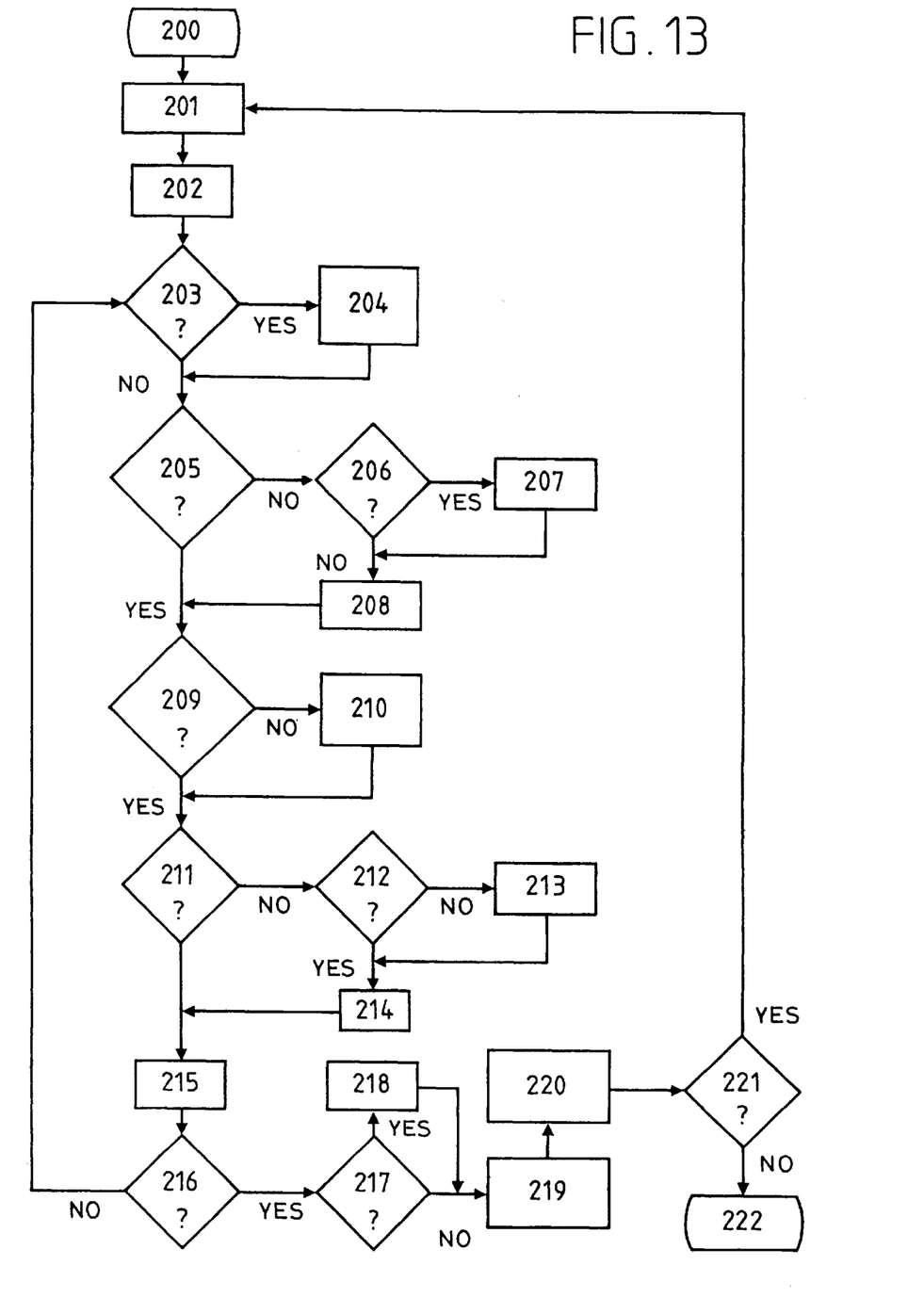
FIG. 13 is a flow chart for carrying out a determination of the topology of an anterior surface of a cornea.

The individual process steps 200 to 222 carried out by the analyzing apparatus 90 for topologically-dependent analysis of the cornea 18 will now be described with reference to FIG. 13 which shows a flow chart of the principal processing steps according to the present invention:

Step 200: Preparation of the keratoscope 20 of the analyzing apparatus 90 for analysis of the cornea.

Step 201: Keratoscope 20 is switched to operating mode for registering topographic data.

Step 202: Keratoscope 20 with the projector 28 and the patient are positionally aligned to one another.

Step 203: Evaluation and decision are made as to whether an image (photo etc.) is taken from the natural topology of the cornea 18 being examined with the probe 33 according to FIG. 7, or without the probe 33 according to FIG. 6.

YES: without probe 33, go to step 204;

NO: with probe, go to step 205.

Step 204: Activation of both electromotive drives 63, 64 for movement of the probe 33 in direction of arrows Y and/or Z into the predetermined position, shown in FIG. 6.

Step 205: Check of the momentary position of the probe 33 with respect to the Y and Z coordinates for compliance with the position necessary for executing the next topologically-dependent image of the cornea 18.

YES: position of the probe 33 is correct, go to step 209;

NO: position of the probe 33 is not correct, go to step 206.

Step 206: Check as to whether contact exists between the probe 33 and the cornea 18.

YES: Contact exits, go to step 207;

NO: No contact, go to step 208.

Step 207: Activation of electromotive drive 62 for withdrawing and detaching the probe 33 from the cornea 18 in direction of arrow X.

Step 208: Activation of both drives 63, 64 for adjustment of the probe 33 in direction of arrows Y and Z.

Step 209: Check as to whether the probe 33 is placed on and contacts the cornea 18.

YES: Contact exits, go to step 211;

NO: No contact, go to step 210.

Step 210: Wait for conclusion of focusing of the keratoscope.

Step 211: Check and decision as to whether the image (photo, etc.) of the topology should be carried out without the probe 33.

YES: go to step 215;

NO: go to step 212.

Step 212: Determination as to whether the probe 33 is placed on the cornea 18.

YES: go to step 214;

NO: go to step 213.

Step 213: Positioning of the probe 33 and placement as well as contacting of the probe on the anterior surface of the cornea 18.

Step 214: Carrying out Indentation of the cornea 18 at the selected site with predetermined values for the force of indentation and/or depth of indentation.

Step 215: Taking of image of the topographic condition of the individual sites in view of the momentary deformation of the cornea 18 as a consequence of the indentation.

Step 216: Check as to whether the predetermined indentation for analysis of the topology of the cornea 18 is realized.

YES: go to step 217;

NO: go back to step 203 and re-execution of the process steps 203 to 215.

Step 217: Check as to whether the probe 33 is still in contact with the cornea 18.

YES: go to step 218;

NO: go to step 219.

Step 218: Withdrawal of the probe 33 by the drive 62 from the cornea 18.

Step 219: Evaluation and optional storage of the individual indentations of the cornea 18 in dependence of the data commensurate with the topology and provided in the form of single or sequential images (photos, film etc.), or in the form of acoustic signals, or combination thereof.

Step 220: Shutting down the keratoscope and returning the keratoscope to its initial position.

Step 221: Evaluation and decision as to whether the topology of the cornea 18 is sufficiently registered and concluded, or whether the keratoscope should be activated for analysis of a next cornea.

YES: Return of the keratoscope 20 to the operation state according to step 201 for carrying out the process steps 203 to 220;

NO: go to step 222.

Step 222: Shutdown of the analyzing apparatus 90.

While the invention has been illustrated and described as embodied in a method of and apparatus for determining the topology of a cornea, it is not intended to be limited to the details shown since various modifications and structural changes may be made without departing in any way from the spirit of the present invention.

What is claimed as new and desired to be protected by letters patent is set forth in the appended claims:

What is claimed is:

1. A method of determining the topology of a cornea, comprising the steps of:

forming a first image of a natural corneal topography;

providing a probe which is program-controlled with depth- or pressure-dependent stored data:

indenting at least one area of the cornea by the probe to effect a momentary deformation of the anterior corneal surface;

forming a second image of the deformation of the anterior corneal surface;

measuring the deformation to produce commensurate topological-dependent data;

processing and storing the data for identifying property of the cornea; and signaling to an operator the data for diagnostic evaluation by at least one unit selected from the group consisting of visual means and acoustic means.

2. The method of claim 1 wherein the deformation of the anterior corneal surface is determined and stored as computer data which is reproducible in the form of a generated image of single frames or a sequence of contiguous frames.

3. The method of claim 1 wherein the second image of the deformation of the anterior corneal surface is formed by generating at least one element selected from the group consisting of acoustic signals and characteristic data.

4. The method of claim 3 wherein the acoustic signals have amplitudes which are measured periodically or intermittently and stored as a sequence of converted digits.

5. The method of claim 3 wherein the acoustic signals are split in deep sounds and high sounds and simulated by a processor for subsequent diagnostic evaluation.

6. The method of claim 1 wherein said indenting step includes advancing the probe in direction of the cornea commensurate with depth-dependent and/or force-dependent data, said measuring step including producing characteristic data of the deformation of the anterior corneal surface in the area of indentation for subsequent diagnostic evaluation.

7. The method of claim 1 wherein said indenting step includes advancing the probe in direction of the cornea in several areas for indentation at different depth and/or force, said individual topographic deformation in the area of the site of indentation being reproducible for diagnostic evaluation of the cornea.

8. The method of claim I wherein said processing step includes forming a combination of data from the stored data of individual indentations analog and in form of single frames and/or sequence of contiguous frames, acoustic signals or characteristic data.

9. The method of claim 1 wherein said indenting step includes advancing the probe in a program-controlled manner in direction of the cornea for indentation at a pre-selected depth.

10. The method of claim 1 wherein said indenting step includes advancing the probe in a program-controlled manner in direction of the cornea for indentation at a pre-selected force.

11. The method of claim 1 wherein said indenting step is executed in dependence on the heartbeat of a patient in a program-controlled and pulse-synchronous manner, said signaling step being realized by visual means and/or acoustic means for subsequent diagnostic evaluation of the cornea.

12. The method of claim 11 wherein said indenting step is realized on several sites of the anterior corneal surface in dependence on a heartbeat of a patient in a program-controlled and pulse-synchronous manner.

13. The method of claim 1 wherein the formed first and second images are ascertained and stored in dependence on a heartbeat of a patient in a program-controlled and pulse-synchronous manner in the area of indentation effected by the probe.

14. The method of claim 1 wherein during and up to conclusion of the indenting step, the force applied by the probe on the anterior corneal surface is electronically monitored and controlled in dependence on a predetermined force.

15. The method of claim 1, and further comprising the steps of withdrawing the probe from the cornea after formation of the second image, and placing the probe in ready position for subsequent indentation of another site on the anterior corneal surface.

16. The method of claim 1 wherein said indenting step includes moving the probe in a first phase in a program-controlled manner towards the anterior corneal surface to a position substantially parallel to a vertical meridian between 90° and 270° or a vertical meridian between 0° and 180°.

17. The method of claim 1 wherein the probe is interacts with an electronically monitored electromagnet that the probe is automatically withdrawn from the effective zone of the electromagnet when experiencing malfunction, to thereby disengage at least the pointed end of the probe from the anterior corneal surface.

18. The method of claim 1 wherein said indenting step includes advancing the probe in the direction of the cornea commensurate with depth-dependent and/or force-dependent data in the selected indentation area, said measuring step including producing the second image of the deformation of the anterior corneal surface in the area of indentation for subsequent diagnostic evaluation.

19. Apparatus for determining topological data of a cornea to be analyzed, comprising:

a positioning device driven by an electromotor;

a mounting having one end secured to the positioning device and another end;

a probe supported by the other end of the mounting and having a pointed end for applying an indentation force on the cornea to realize a deformation of the anterior corneal surface, said probe being program controlled with depth- or pressure dependent data from which the topology of the cornea can be determined;

an electromagnet positioned between the mounting and the probe and so interacting with the probe as to withdraw the probe from a sphere of influence of the electromagnet to thereby disengage the pointed end from the anterior corneal surface when the indentation force exceeds a predetermined level; and detection means for determining and measuring a deformation of the anterior corneal surface realized by the probe during indentation of the cornea.

20. The apparatus of claim 19 wherein the mounting includes a bracket having one end for attachment of the electromagnet and another end secured to the positioning device.

21. The apparatus of claim 20 wherein the bracket is of 90° Z-shaped configuration.

22. The apparatus of claim 20 wherein the mounting includes a support arm having one end for attachment of the probe which extends into the projector, and another end for securement to the electromagnet.

23. The apparatus of claim 22, and further comprising a ferromagnetic plate positioned between the other end of the support arm and the electromagnet.

24. The apparatus of claim 22, and further comprising a pair of spaced supports for connecting the other end of the support arm to the bracket, and further comprising a first force sensor mounted to one of the supports and interacting with the electromagnet.

25. The apparatus of claim 24, and further comprising a second force sensor mounted to the other one of the supports and interacting with the electromagnet, said first and second force sensors so interacting with the electromagnet that the support arm is shifted to the electromagnet when the indentation force applied by the probe exceeds a predetermined level.

26. The apparatus of claim 19 wherein the support arm and the attached probe are made of electrically conductive material.

27. The apparatus of claim 19, and further comprising an adjustable platform unit mounted to the detection means and supporting the positioning device, and a support frame for placement of a patient's head in alignment with the projection cone of the keratoscope, said support frame having at least one hand grip, a first sensor received in the hand grip for actuation by the patient, a forehead support, and a second sensor received in the forehead support.

28. The apparatus of claim 27 wherein the platform unit includes a first plate, a second plate mounted to and positioned at a distance above the first plate for supporting the positioning device, and supports for connecting the first plate to the detection means.

29. The apparatus of claim 28 wherein the second plate is swingably mounted to the first plate for rotation about a pivot axis extending transversely to an optic axis of the detection means to thereby allow adjustment of the probe relative to the optic axis.

30. The apparatus of claim 27, and further comprising an evaluation means including a detector unit, an interface unit operatively connected to the detector unit, and a processor operatively connected to the interface unit, each of said detector unit, said interface unit and said processor having incorporated therein electronic means for determining and processing the topology-dependent data of the cornea, said detector unit being operatively connected to the first and second sensors.

31. The apparatus of claim 19 wherein the detection means includes a video keratoscope.

32. The apparatus of claim 19, and further comprising an evaluation means including a detector unit, an interface unit operatively connected to the detector unit, and a processor operatively connected to the interface unit, each of said detector unit, said interface unit and said processor having incorporated therein electronic means for determining and processing the topology-dependent data of the cornea.

33. The apparatus of claim 32 wherein the detector unit is operatively connected to the probe.

34. The apparatus of claim 33, and further comprising a force sensor positioned between the detector unit and the probe.

35. The apparatus of claim 34 wherein the electromagnet has a magnetic coil, said processor including a controller module having incorporated therein electronic means for reading information outputted by the force sensor to thereby adjust the electric current across the magnetic coil.

36. The apparatus of claim 33, and further comprising two force sensors positioned separately from one another between the detector unit and the probe.

37. The apparatus of claim 32 wherein the interface unit is operatively connected to the positioning device.

38. The apparatus of claim 32, and further comprising a color printer operatively connected to the processor for printing determined topological data during analysis of the cornea in the form of single frames or sequence of contiguous frames.

39. The apparatus of claim 32, and further comprising a color monitor for visual colored illustration of determined topological data during analysis of the cornea.

40. The apparatus of claim 32 wherein the electromagnet is excited by electric current which is adjustable by the processor.

41. The apparatus of claim 32 wherein the electromagnet is excited by a preselected and adjustable electric current.

42. The apparatus of claim 32 wherein the processor has incorporated therein electronic means for adjusting an indentation force applied by the probe on the anterior corneal surface.

* * * * *